United States Patent [19]

Kallok et al.

[11] Patent Number: 5,211,173
[45] Date of Patent: May 18, 1993

[54] SERVO MUSCLE CONTROL

[75] Inventors: Michael J. Kallok, New Brighton; Brian B. Lee, Golden Valley, both of Minn.

[73] Assignee: Medtronic, Inc., Minneapolis, Minn.

[21] Appl. No.: 947,826

[22] Filed: Sep. 21, 1992

Related U.S. Application Data

[63] Continuation of Ser. No. 639,192, Jan. 9, 1991, abandoned.

[51] Int. Cl.⁵ .............................................. A61N 1/36
[52] U.S. Cl. .............................................. 128/419 G
[58] Field of Search ................ 128/419 G, 716, 720, 128/724, 204.23

[56] References Cited

U.S. PATENT DOCUMENTS 4,969,467 11/1990 Callaghan et al. ........... 128/419 PG

FOREIGN PATENT DOCUMENTS 8600234 1/1986 PCT Int'l Appl. .

Primary Examiner—Kyle L. Howell
Assistant Examiner—Kennedy J. Schaetzle
Attorney, Agent, or Firm—Harold R. Patton; Daniel W. Latham; John L. Rooney

[57] ABSTRACT

A method of and apparatus for controlling one or more parameters of an electrical stimulation generator in response to measured results of the stimulation. In the preferred mode, this technique is employed in a system for the treatment of obstructive sleep apnea. Sensors are used to determine the effectiveness of the stimulation. Amplitude and pulse width are modified in response to the measurements from the sensors.

11 Claims, 7 Drawing Sheets

SERVO MUSCLE CONTROL

This is a continuation of co-pending application Ser. No. 07/639,192 filed on Jan. 9, 1991 now abandoned.

CROSS REFERENCE TO CO-PENDING APPLICATIONS

U.S. patent application Ser. No. 07/610,854, filed Nov. 8, 1990, now U.S. Pat. No. 5,133,354, and entitled "Improving Muscle Tone"; and U.S. patent application Ser. No. 07/617,158, filed Nov. 23, 1990, now abandoned and entitled "Multiple Stimulation Electrodes" are both assigned to the assignee of the present invention.

BACKGROUND OF THE INVENTION

1. Field of the Invention

The present invention generally relates to electrical stimulation of muscles, and more particularly, relates to electrical stimulation of muscles for the treatment of a medical condition.

2. Description of the Prior Art

It has been known to electrically stimulate muscular contractions since the beginnings of experimentation with electricity. In more recent times, electrical stimulation of muscle tissue has been used therapeutically. The effects of chronic stimulation have been studied by Ciske and Faulkner in "Chronic Electrical Stimulation of Nongrafted and Grafted Skeletal Muscles in Rats", in *Journal of Applied Physiology*, Volume 59(5), pp. 1434–1439 (1985). Bernotas et al., have even suggested the rudiments of adaptive control in "Adaptive Control of Electrically Stimulated Muscle", in *IEEE Transactions on Biomedical Engineering*, Volume BME-34, No. 2, pp. 140-147, (February, 1987).

A review of early attempts at electrical stimulation associated with the respiratory system is found in "Diaphragm Pacing: Present Status", by William W. L. Glenn, in *Pace*, Volume 1, pp. 357-370, (July–September, 1978). Much work has been done in electrical stimulation within the cardiovascular system by way of cardiac pacing.

Treatment of obstructive sleep apnea using electrical stimulation has also been discussed. "Laryngeal Pacemaker, II Electronic Pacing of Reinnervated Posterior Cricoarytenoid Muscles in the Canine", by Broniatowski et al, in *Laryngoscope*, Volume 95, pp. 1194-1198 (October, 1985); "Assessment of Muscle Action on Upper Airway Stability in Anesthetized Dogs", by Strohl et al., in *Journal of Laboratory Clinical Medicine*, Volume 110, pp. 221-301, (1987); U.S. Pat. No. 4,830,008 issued to Meer; and U.S. Pat. No. 4,570,631 issued to Durkan all discuss electrical stimulation of the upper airway to treat obstructive sleep apnea.

SUMMARY OF THE INVENTION

The present invention overcomes the disadvantages of the prior art by providing a system for the electrical stimulation of muscle tissue, which is adaptive in nature. Sensors are employed within the stimulation system to modify parameters such as stimulation pulse amplitude and pulse frequency in response to the sensed performance of the therapy desired.

In the preferred mode, the present invention is applied to the treatment of obstructive sleep apnea. Sensors are employed to determine the pressure differential between the distal pharynx and the ambient to determine the pressure drop across the upper airway. Stimulation intensity is increased as the relative pressure differential increases, and decreased as the relative pressure differential decreases. Intensity may be increased by increased pulse frequency and/or pulse amplitude. Additional sensing is required to accommodate the respiration cycle, permitting the system to adapt independent of the normal cyclic variations.

There are a number of important results attendant to the adaptive system. The total energy required is lessened, because the stimulation intensity is maintained at only that level necessary to sustain the desired clinical performance. The risk of muscle fatigue is greatly reduced because the muscles of the upper airway are not over stimulated. Similarly, the lack of over stimulation provides the patient with a more easily tolerated therapy, particularly when used chronically.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
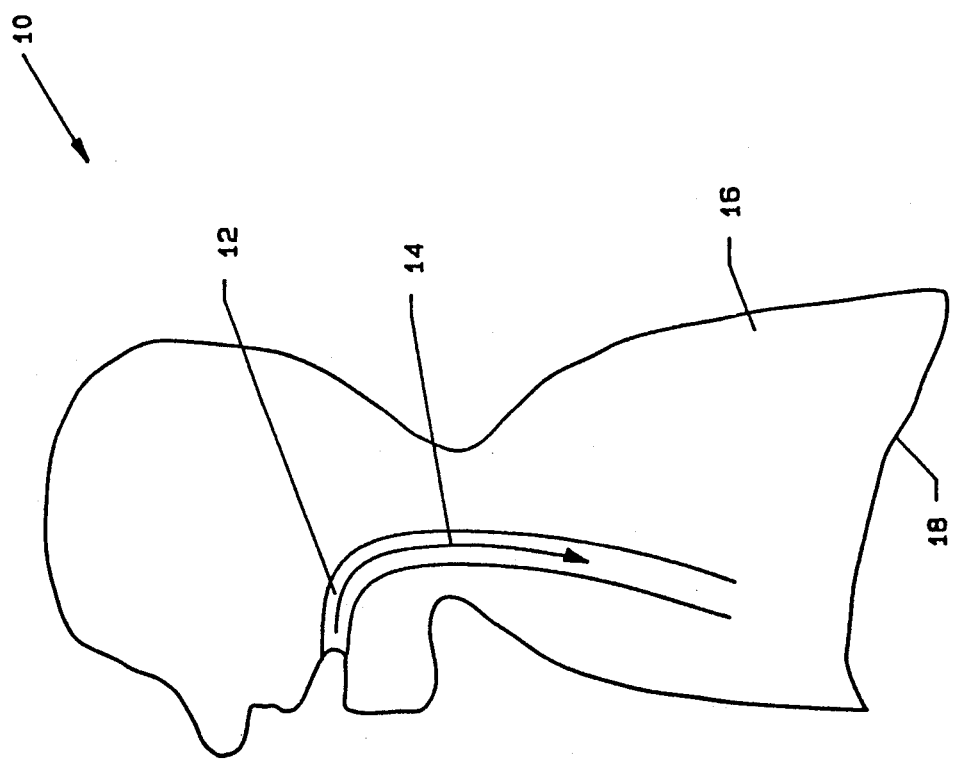
FIG. 1 is a schematic diagram of the normal function of the respiration system of a patient during inspiration.

FIG. 1 is a schematic diagram of the respiratory system of patient 10 during inspiration. As a result of diaphragm 18 increasing the volume of thorax 16, a pressure differential is created causing air to enter upper airway 12 and proceed in the direction of arrow 14.

Figure 2:
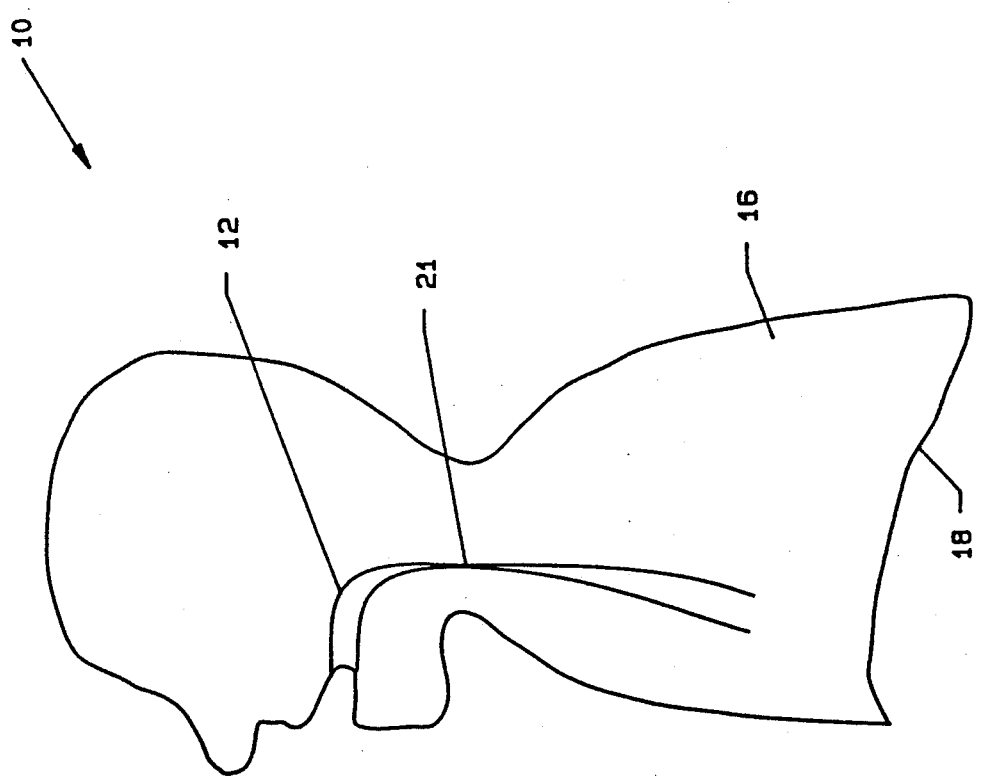
FIG. 2 is a schematic diagram of the same patient with obstructive sleep apnea.

FIG. 2 is a schematic diagram of the respiratory system of patient 10 during an obstructive apnea event. During inspiration, upper airway 12 tends to collapse producing the obstruction to air flow at point 21. The above-referenced literature describes in detail the physiological processes associated with the collapse of upper airway 12.

Figure 3:
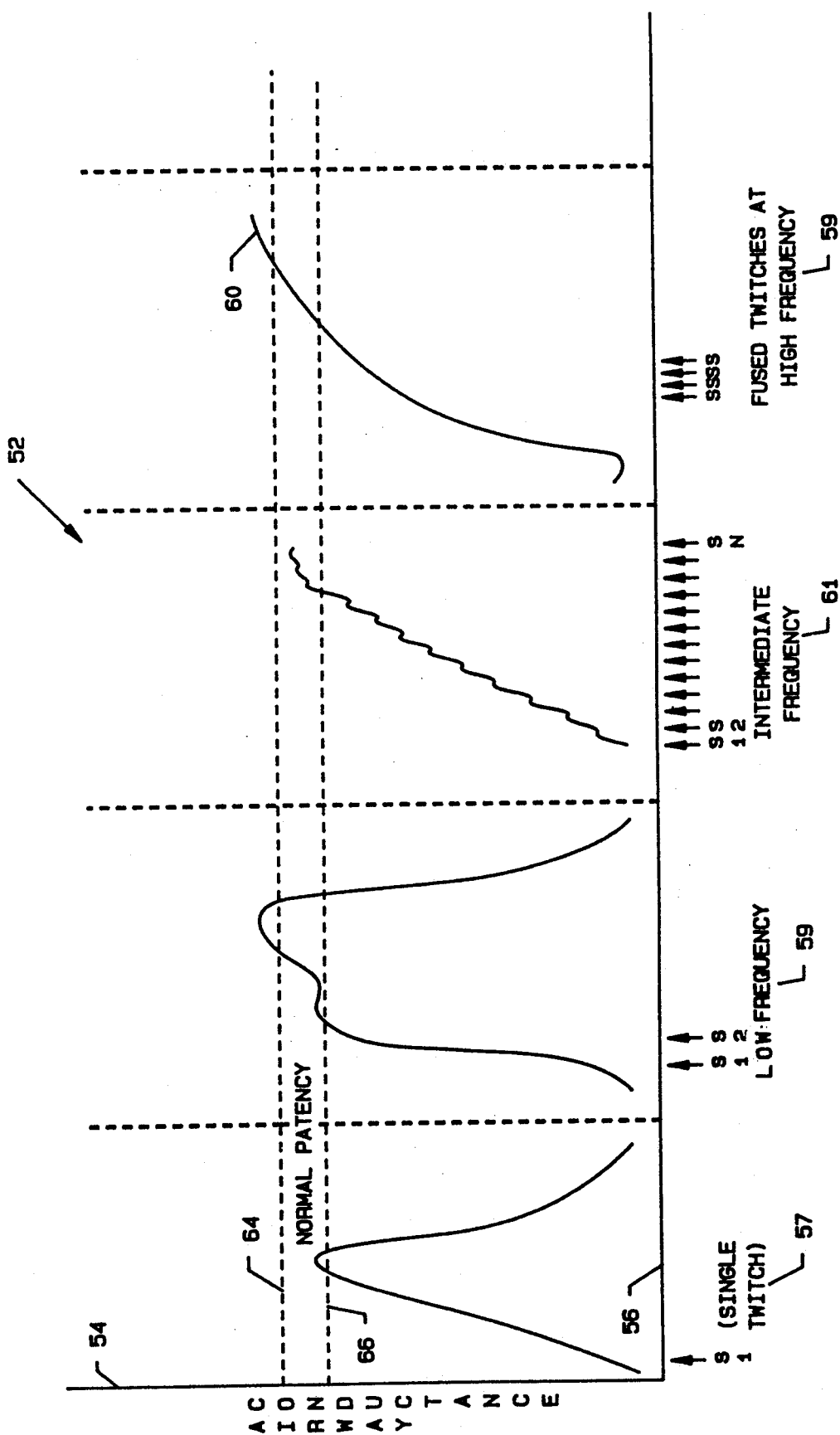
FIG. 3 is a graphical representation of airway conductance versus stimulation level in a patient with obstructive sleep apnea.

FIG. 3 is a graphical representation 52 of airway conductance 54 as a function of stimulation frequency 56 in patient 10 suffering from obstructive sleep apnea. At single twitch (57) or relatively low level stimulation frequency 59, airway conductance 54 is insufficient as shown along the corresponding portions of the curve. Single twitch and low frequency stimulation do not sustain conductance change (i.e., sufficient tension) and result in tension plateaus which are too low to maintain an open airway. Normal patency is airway conductance between levels 64 and 66. To achieve normal patency, stimulation frequency must be at least as point 61.

For stimulation frequency greater than that for normal patency (i.e. airway conductance 54 of greater than level 64), very little improvement can be observed. Portion 60 of the curve represents this state. As the system proceeds along portion 60, stimulation frequency is excessive resulting in wasted energy and increased risk of muscle fatigue.

Figure 4:
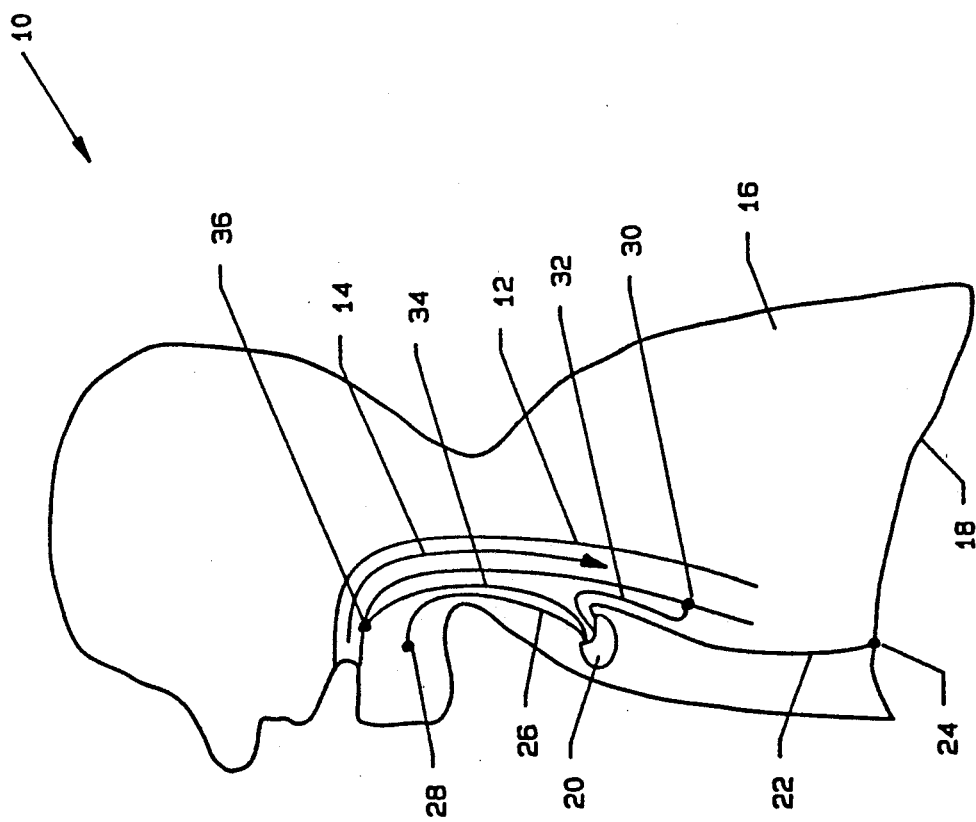
FIG. 4 is a schematic diagram of a patient having an electrical stimulation system employing the present invention.

FIG. 4 is a schematic diagram of patient 10 showing implantation of an electrical stimulation system for the treatment of obstructive sleep apnea. Implantable pulse generator 20 is placed subcutaneously at a convenient position. The operation of diaphragm 18 is monitored by electrode 24 coupled to lead 22.

Patency of upper airway 12 is monitored by pressure sensor 36 and pressure sensor 30 coupled to implantable pulse generator 20 via cables 34 and 32, respectively. Stimulation of the musculature of upper airway 12 is accomplished via lead 26 coupled to electrode 28. All other referenced elements are as previously described.

Figure 5:
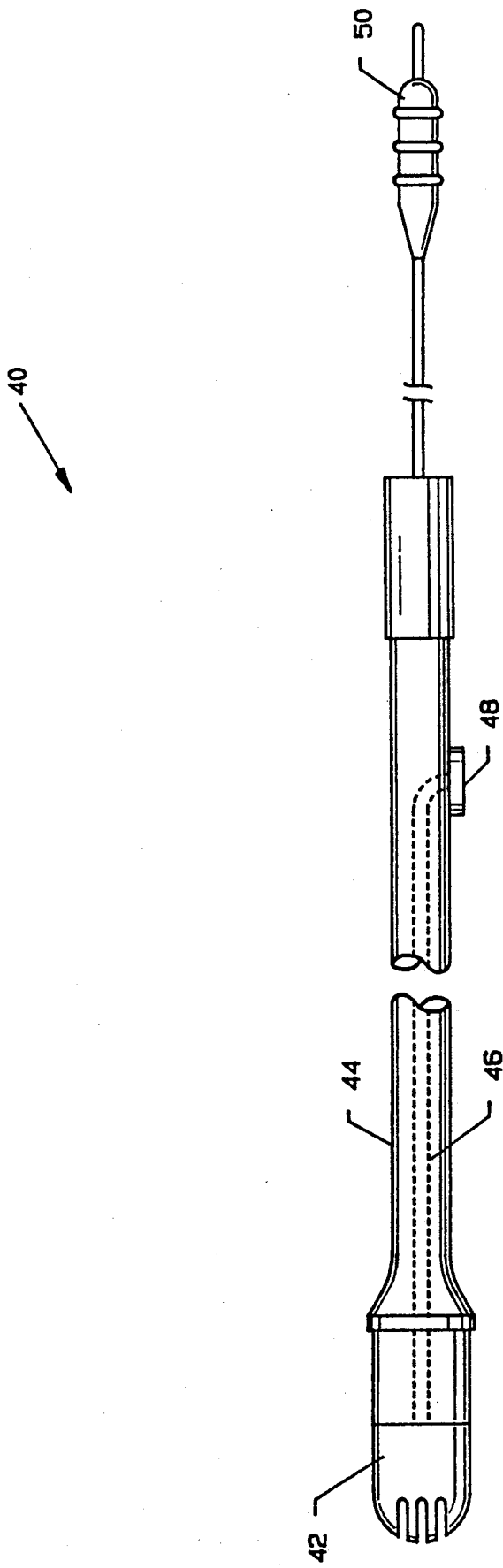
FIG. 5 is a plan view of a chronically implantable pressure sensor.

FIG. 5 is a plan view of a chronically implantable pressure transducer 40 similar to that implanted as pressure sensors 30 and 36 (see also FIG. 4). Distal end 42 of chronically implantable pressure transducer 40 contains a semiconductor sensing element properly package for chronic implantation. Lead body 44 optionally contains pressure reference lumen 46, which is coupled to pressure vent 48. Electrical connector 50 couples to implantable pulse generator 20. For additional construction details, the reader may consult U.S. Pat. No. 4,407,296 issued to Anderson incorporated herein by reference.

Figure 6:
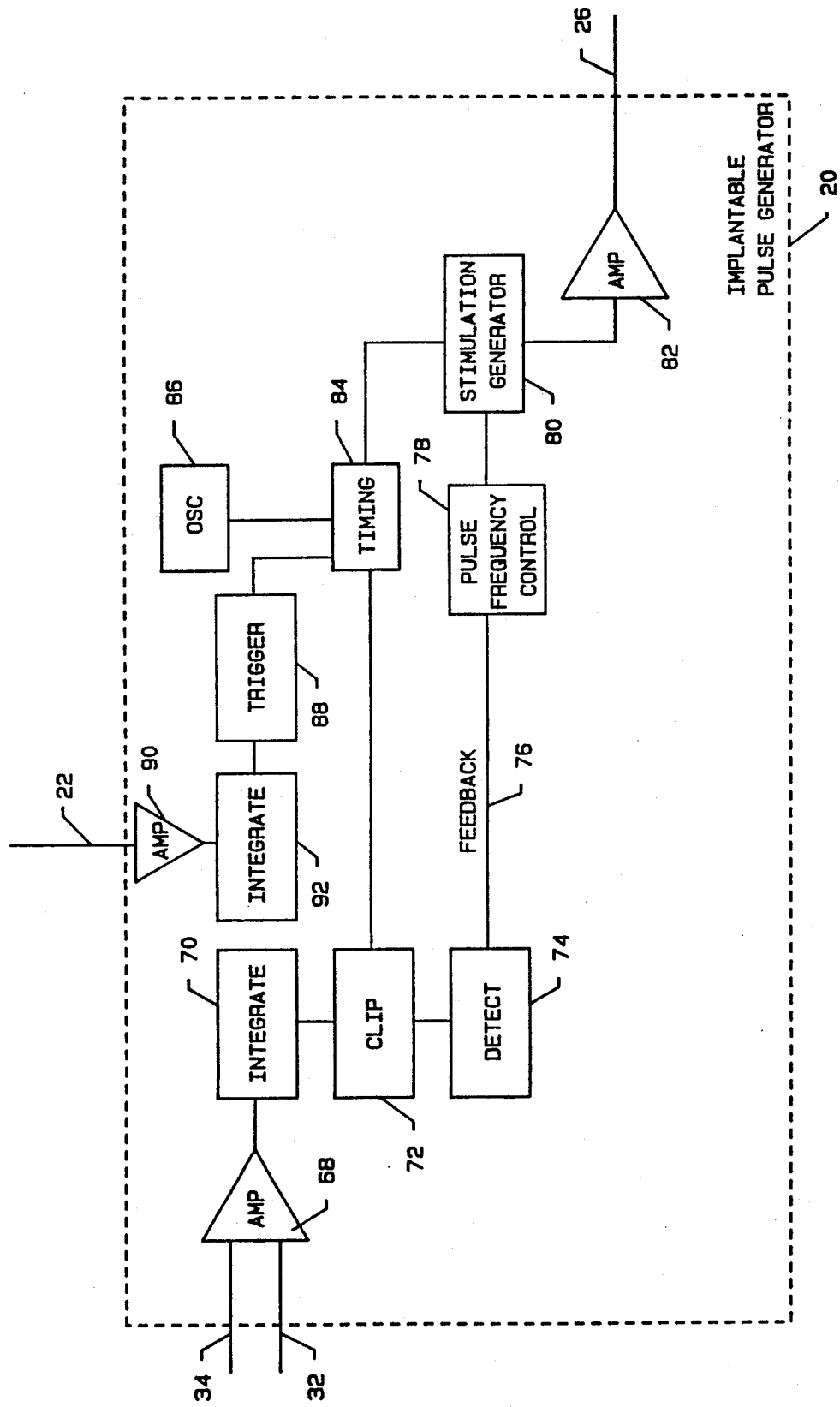
FIG. 6 is a block diagram of an implantable pulse generator according to the present invention; and, FIG. 7 is a graphical representation of the key signals within the implanted electrical stimulation system.

FIG. 6 is a block diagram of implantable pulse generator 20 made in accordance with the present invention. Cables 32 and 34, coupled to pressure sensors 30 and 36, respectively, provide the inputs to differential amplifier 68. The output of differential amplifier 68 is thus representative of the pressure differential between the pharynx and the mouth (see also FIG. 4).

The pressure difference signal is integrated by integrator 70 to provide a smooth signal. The signal is clipped by clipper circuit 72 to scale the signal. Detector 74 is a thresholding device. The output of detector 74 is essentially a binary feedback signal 76 indicative of whether upper airway 12 has sufficient patency. Binary feedback signal 76 is used to control pulse frequency control 78. In this way, the pulse frequency of the stimulation pulses is continually increased until sufficient patency is monitored. Pulse frequency control 78 may also change output amplitude of the stimulation pulses. The stimulation pulses are produced by stimulation generator 80, amplified by amplifier 82, and coupled to the upper airway musculature by amplifier 82.

The stimulation pulses generated are timed in accordance with the respiration cycle by timing 84. This circuit also notifies clipper circuit 72 of the time window in which patient 10 is within an inspiration cycle. Timing 84 operates by drive from oscillator 86, which is the main timing standard within implantable pulse generator 20.

The position within the respiration cycle is monitored by electrode 24 coupled to lead 22 (see also FIG. 4). Other means can also be used to sense inspiration, such as impedance plethysmography. In the preferred mode, it is the EMG which is actually sensed. The EMG is amplified by amplifier 90 and integrated by integrator 92. This smooths the signal considerably. The integrated signal is supplied to trigger 88, which is a thresholded monostable multivibrator. The output of trigger 88 is a fixed length signal having a leading edge occurring at the initiation of an inspiration cycle. As explained above, timing 84 synchronizes the output of trigger 88 with the output of oscillator 86 and provides time windows to clipper circuit 72 and stimulation generator 80.

Figure 7:
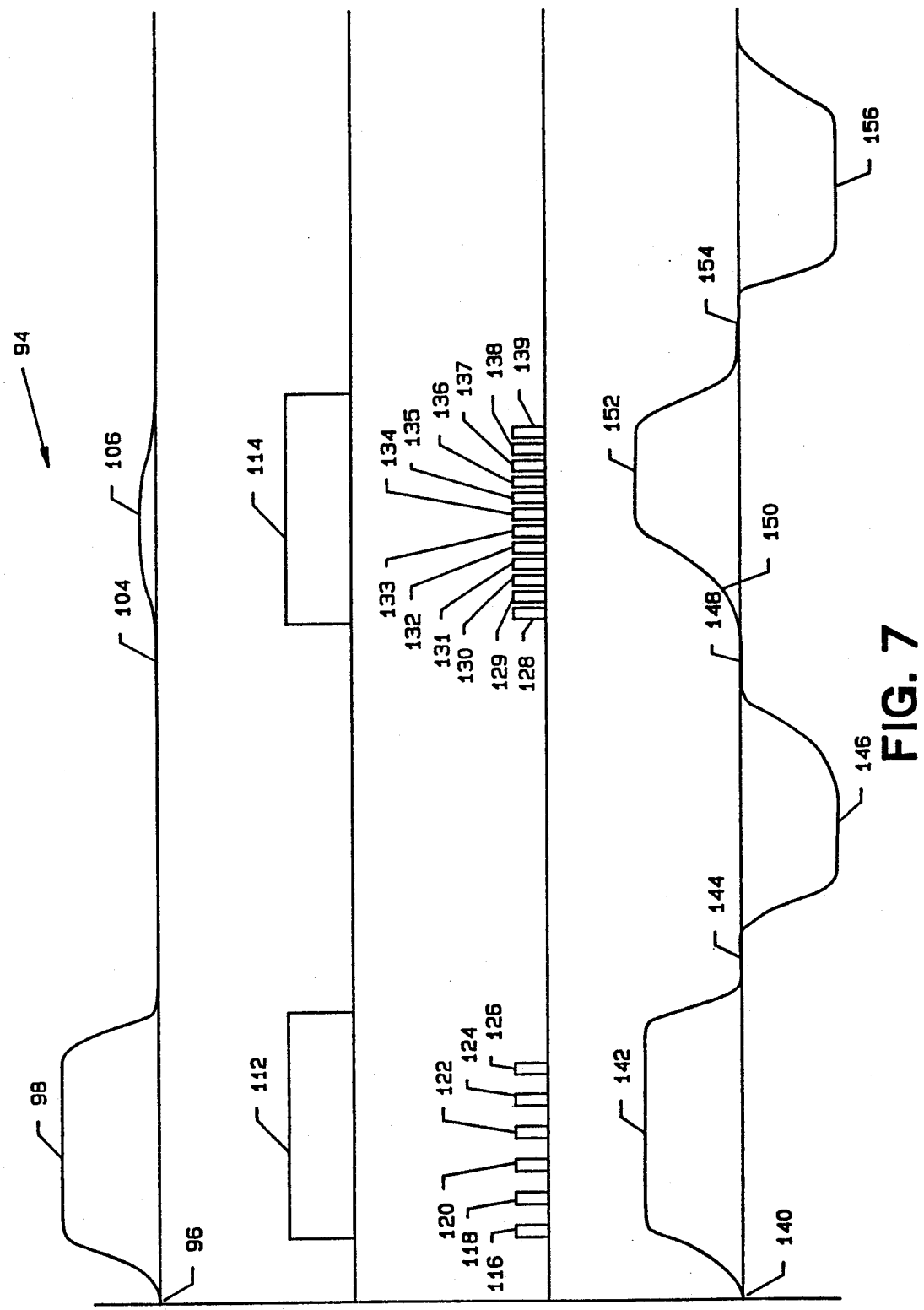

FIG. 7 is a graphical representation 94 of various key signals of implantable pulse generator 20. Curve 96 shows the pressure differentials to be monitored for two respiratory cycles wherein the first cycle involves a substantial obstruction within upper airway 12, and the second cycle shows normal patency as a result of electrical stimulation of sufficient intensity. Portion 98 of curve 96 is the pressure differential resulting from inspiration with an obstructed upper airway.

Pressure differential 106 follows null period 104. Pressure differential 106 shows inspiration under normal patency because the stimulation intensity has been increased.

Pulses 112 and 114 are the output of trigger 88 (see also FIG. 6). They provide the timing window associated with the inspiration portion of the respiratory cycle. Stimulation pulses 116, 118, 120, 122, 124, and 126 are supplied during the first inspiration. As seen above, the frequency of these stimulation pulses is insufficient to produce normal patency of the upper airway. The feedback system ensures that the pulse frequency of succeeding stimulation pulses 128, 129, 130, 131, 132, 133, 134, 135, 136, 137, 138, and 139 is greater. In this case, the stimulation frequency is sufficient to produce normal patency as is seen in pressure differential 106.

Curve 140 shows the output of integrator 92 (see also FIG. 6). It is from curve 140 that trigger 88 generates pulses 112 and 114. Peaks 142 and 152 correspond to the inspiration periods. Similarly, negative peaks 146 and 156 correspond to the expiration periods. Null periods 144, 148, and 154 separate portions of the respiratory cycle. Note that slope 150 will be effected by the increase in stimulation intensity from respiratory cycle one to respiratory cycle two.

Having thus described the preferred embodiments of the present invention, those of skill in the art will readily appreciate the other variations possible within the teachings found herein and within the scope of the claims hereto attached.

I claim:

1. A method of treating obstructive sleep apnea in a patient comprising:
   a. monitoring the respiratory cycle of said patient to determine the inspiration portion;
   b. generating stimulation pulses corresponding with said inspiration portion of said respiration cycle;
   c. monitoring upper airway patency during said inspiration portion of said respiration cycle; and,
   d. adjusting the intensity of said stimulation pulses in response to the results of said upper airway patency monitoring step to maintain normal patency of said upper airway.

2. A method according to claim 1 wherein said monitoring upper airway patency further comprises measuring pressure differential during said inspiration portion of said respiratory cycle.

3. A method according to claim 2 wherein said adjusting further comprises changing pulse frequency of said stimulation pulses.

4. A method according to claim 2 wherein said adjusting further comprises changing amplitude of said stimulation pulses.

5. A method according to claim 3 wherein said adjusting further comprises changing amplitude of said stimulation pulses.

6. An apparatus for treating obstructive sleep apnea comprising:
   a. means for generating signals to stimulate upper airway muscle tissue of a patient;
   b. means coupled to said generating means for timing said signals to produce stimulation of said upper airway muscle tissue during inspiration by said patient;
   c. means for monitoring efficacy of stimulation of said signals; and,
   d. means coupled to said monitoring means and said generating means for adjusting intensity of said signals to efficiently increase patency of said upper airway of said patient.

7. An apparatus according to claim 6 wherein said monitoring means comprises means for measuring temperature differential across said upper airway of said patient.

8. An apparatus according to claim 6 wherein said adjusting means comprises means for changing pulse frequency of said signals.

9. An apparatus according to claim 7 wherein said adjusting means comprises means for changing pulse frequency of said signals.

10. An apparatus according to claim 6 wherein said adjusting means comprises means for changing amplitude of said signals.

11. An apparatus according to claim 7 wherein said adjusting means comprises means for changing amplitude of said signals.

* * * * *